United States Patent [19]
Fletcher et al.

[11] 4,030,348

[45] June 21, 1977

[54] MACHINE FOR USE IN MONITORING FATIGUE LIFE FOR A PLURALITY OF ELASTOMERIC SPECIMENS

[76] Inventors: James C. Fletcher, Administrator of the National Aeronautics and Space Administration, with respect to an invention of; George E. Fitzer, Arcadia, Calif.

[22] Filed: Jan. 29, 1976

[21] Appl. No.: 653,682

[52] U.S. Cl. .................................. 73/91; 73/15.6
[51] Int. Cl.² ........................................ G01N 3/34
[58] Field of Search ................. 73/91, 15.6, 67.3

[56] References Cited
UNITED STATES PATENTS

| | | | |
|---|---|---|---|
| 1,499,546 | 7/1924 | Oxley | 73/91 |
| 3,535,921 | 10/1970 | Smiley | 73/91 |

*Primary Examiner*—Jerry W. Myracle
*Attorney, Agent, or Firm*—Monte F. Mott; Wilfred Grifka; John R. Manning

[57] ABSTRACT

An improved machine for use in determining the fatigue life for elastomeric specimens. The machine is characterized by a plurality of juxtaposed test stations, specimen support means located at each of the test stations for supporting a plurality of specimens of elastomeric material and means for subjecting the specimens at each of said stations to sinusoidal strain at a strain rate unique with respect to the strain rate at which the specimens at each of the other stations is subjected to sinusoidal strain.

8 Claims, 5 Drawing Figures

MACHINE FOR USE IN MONITORING FATIGUE LIFE FOR A PLURALITY OF ELASTOMERIC SPECIMENS

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

BACKGROUND OF THE INVENTION

1. Field of the Invention

The invention generally relates to devices for testing the durability of elastomeric materials and more particularly to an improved testing machine for use in determining the duration of fatigue life for a plurality of elastomeric specimens simultaneously subjected to cyclic strain over a range of frequencies.

The fatigue life for elastomeric materials often is determined by employing mechanical devices which cyclically subject specimens to tensile stress, whereby failure of the stressed specimens serves to indicate the term of fatigue life for the specimens. Normally, the term of fatigue life for a specimen is dictated by factors such as test temperatures, strain amplitude and strain rate.

2. Description of the Prior Art

The prior art, of course, includes numerous devices for use in subjecting samples of elastomeric materials to destructive strain, whereby the term of fatigue life for a given elastomeric specimen is determined. However, machines currently available are economically expensive and impractical as they are incapable of use in simultaneously subjecting a plurality of specimens to strain at different strain rates and amplitudes. For example, in the aerospace industry it often becomes necessary to determine with precise accuracy the term of fatigue life for a given elastomeric material at various strain rates and amplitudes, in order to establish parameters for optimum performance and thus assure completion of a mission. As a consequence, a large number of tests are required which, in turn, requires that a large number of expensive testing machines be employed simultaneously, often for terms of impractical durations. Hence, there exists a need for a practical and economic machine adapted to be employed in determining the term of fatigue life for a plurality of elastomeric specimens simultaneously subjected to cyclic strain at selected amplitudes and strain rates varying over a desired range of frequencies.

It is, therefore, the general purpose of the instant invention to provide an improved practical and economic testing machine through the use of which the term of fatigue life for elastomeric specimens can be determined in a temperature-controlled environment, at variable amplitudes and strain rates varying over a wide frequency range.

OBJECTS AND SUMMARY OF THE INVENTION

It is, therefore, an object of the instant invention to provide a machine for use in determining fatigue life for elastomeric specimens which overcomes the aforementioned difficulties and disadvantages.

Another object is to provide an improved machine for use in determining the term of fatigue life of elastomeric specimens in a temperature-controlled environment.

Another object is to provide a machine for use in determining fatigue life for elastomeric specimens having a capability of simultaneously subjecting elastomers to cyclic strain over a selected frequency range.

Another object is to provide a machine for determining fatigue life for a plurality of elastomeric specimens supported in a temperature-controlled environment by simultaneously subjecting the specimens to cyclic strain at variable strain rates and strain amplitudes.

It is another object to provide a machine for determining fatigue life for a plurality of elastomeric specimens, derived from a common elastomeric material, confined in a temperature-controlled environment and subjected to cyclic strain at variable strain amplitudes and strain rates extending over a wide frequency range, although not necessarily limited in use thereto since the machine is useful in determining the fatigue life for elastomeric specimens derived from different materials and subjected to common strain rates at fixed amplitudes.

These and other objects and advantages are achieved through the use of a machine having a plurality of test stations arranged in juxtaposition within a hermetically sealable chamber, specimen support means located at each of the test stations for supporting in suspension a plurality of elastomeric specimens, and tensioning means arranged in coplanar relation with the specimen support means at each of the stations for periodically applying to the specimens tensile forces of a variable magnitude at frequencies differing by a selected factor for cyclically subjecting the specimens to sinusoidal strain of selected magnitudes over a given range of frequencies.

DESCRIPTION OF THE PREFERRED EMBODIMENT

Figure 1:
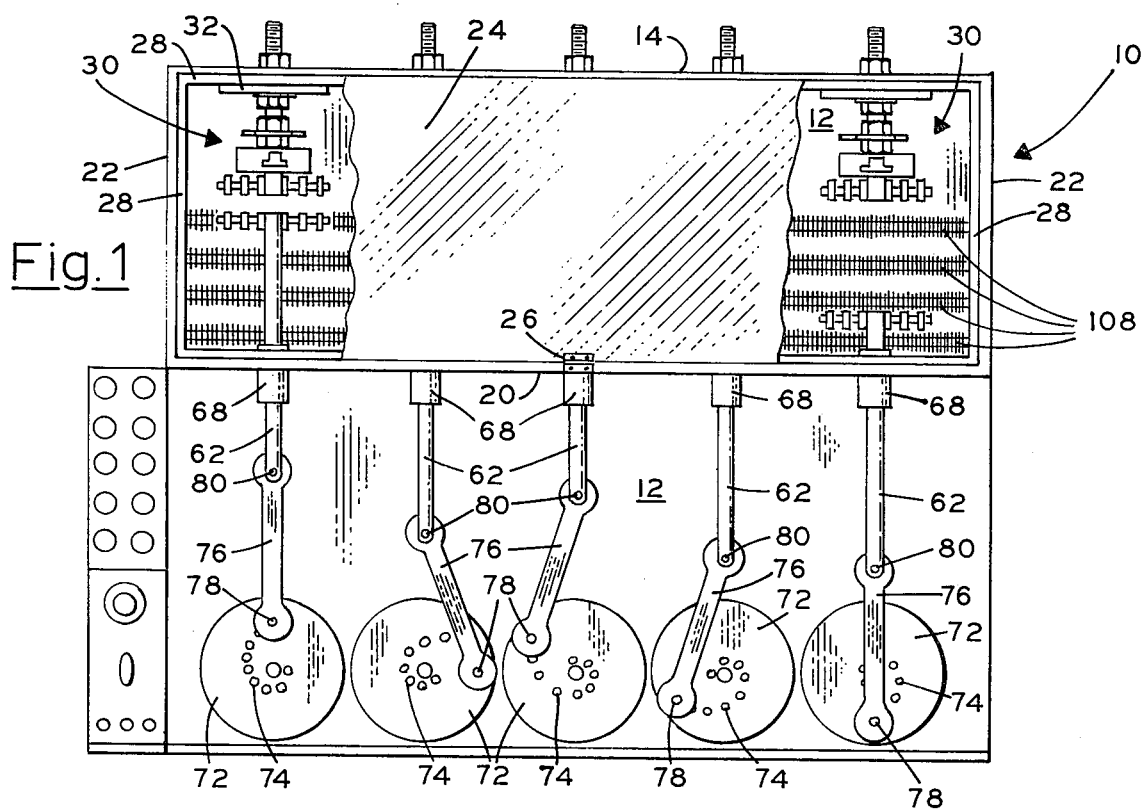
FIG. 1 is a fragmented front view of a machine, which embodies the principles of the instant invention, including a plurality of test stations provided for subjecting elastomeric specimens to cyclic strain in a temperature-controlled environment.
Figure 2:
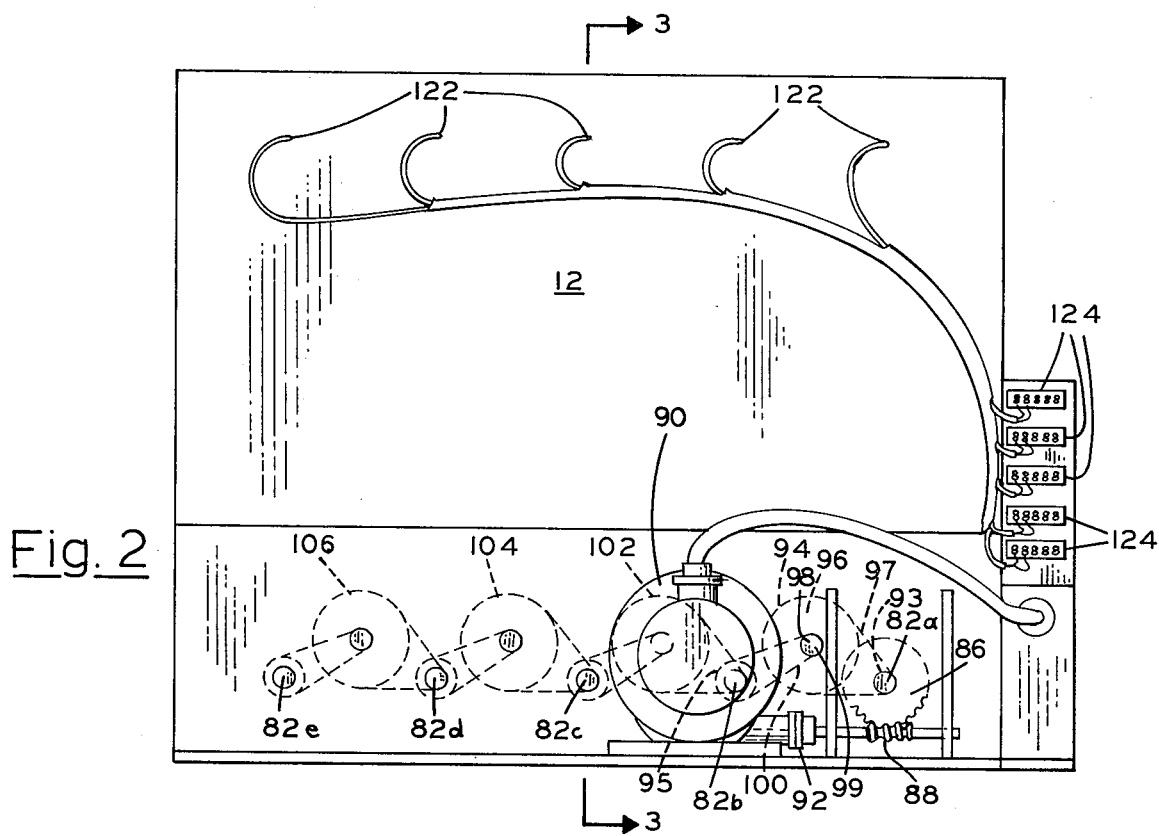
FIG. 2 is a rear view of the machine.

Referring now to the drawings wherein like reference characters designate like or corresponding parts throughout the several views, there is shown in FIG. 1 a machine, generally designated 10, which embodies the principles of the instant invention.

The machine 10 includes a rear wall 12 and a top wall 14, supported by a base plate 16 from which the rear wall is vertically projected. Immediately beneath the top wall 14 there is a hermetically sealable chamber 18. This chamber is defined by a bottom chamber wall 20 arranged in spaced parallelism with the top wall 14 and a pair of end walls 22. The chamber 18 is closed by a closure panel 24 formed of a suitable transparent material. As a practical matter, the closure panel 24 is supported by a plurality of hinges 26 and seats against a door stop 28 provided about the periphery of the chamber. The door stops 28 are so configured as to establish a substantially hermetic seal for the chamber 18, upon the closing of the closure panel 24 for facilitating an establishment of a temperature-controlled environment within the chamber.

Arranged in juxtaposed alignment within the chamber 18 is a plurality of test stations, each being generally designated 30. As shown in the drawings, five such stations are provided, however, it is to be understood that the number of stations can be varied as desired.

At each of the stations 30 there is provided a mounting bracket 32 affixed to and supported by the rear wall 12. Each of the mounting brackets 32, as a practical matter, includes a pair of plates arranged in angularly related planes and interconnected through a gusset, not designated. The mounting brackets 32 are secured to the rear wall 12 and the top wall 14 employing suitable fasteners, not shown.

Since the test stations are of a common design and function in a similar manner to achieve a similar result, a detailed description of a single one of the test stations is believed adequate to provide for a complete understanding of the invention.

Figure 3:
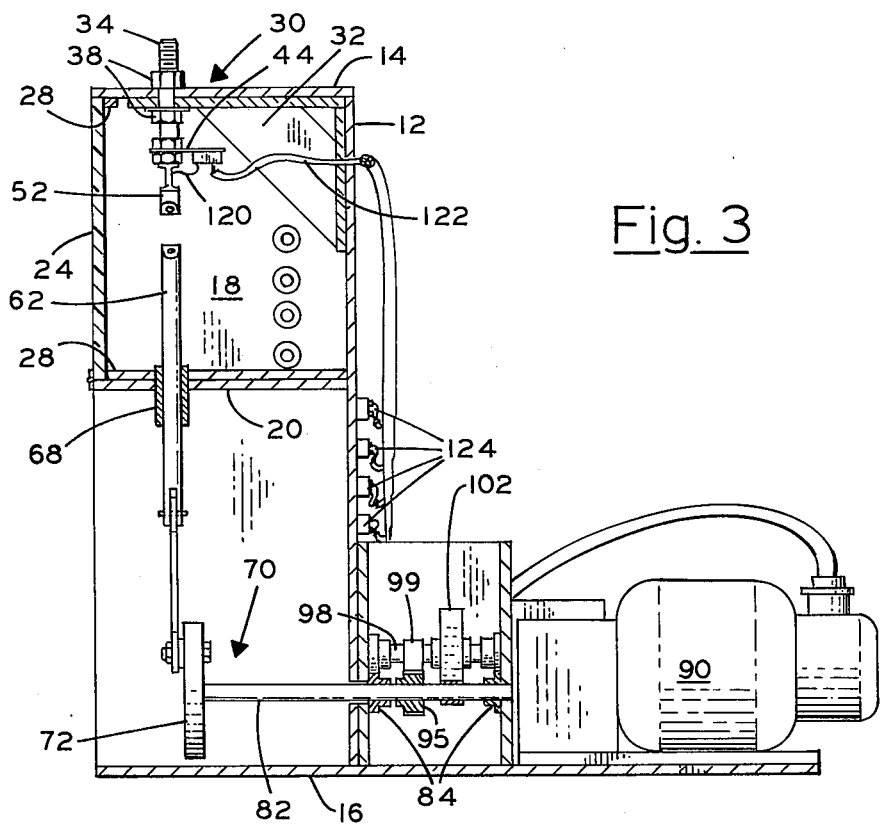
FIG. 3 is a cross-sectional view, taken generally along line 3—3 of FIG. 2.
Figure 4:
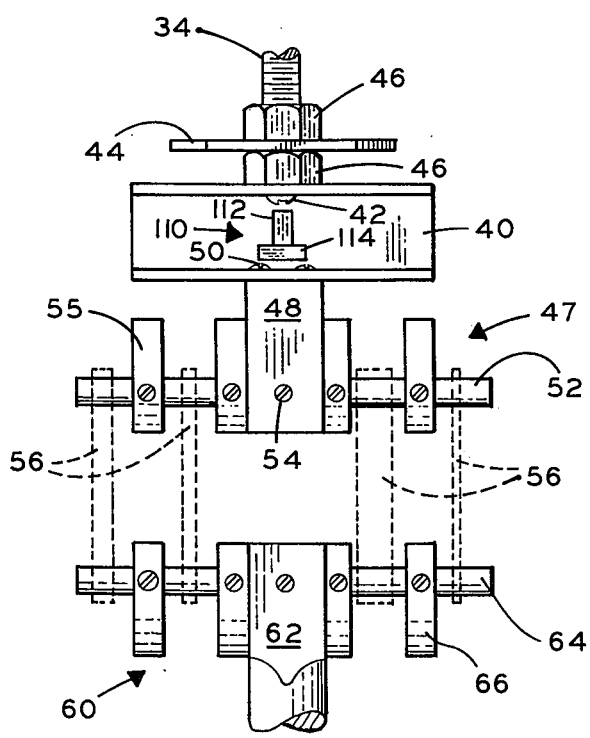
FIG. 4 is a fragmented view of one of the test stations shown in FIG. 1.

As best illustrated in FIG. 3, each of the test stations 30 includes a vertically oriented hanger rod 34. The hanger rod 34 is externally threaded throughout its length and is supported by a pair of jam nuts 36 and 38 arranged at opposite sides of the top wall 14. Supported in suspension by the hanger rod 34 is a horizontally extended support member 40 formed of a suitable material, such as aluminum or the like. The support is characterized by an I-beam configuration, and is connected to the hanger rod 34 by a screw 42 vertically extended through a flange of the support member and received within an axially extended, internally threaded bore, not designated, provided within the hanger rod.

Also mounted on the hanger rod 34 is a plate 44 secured in place by a pair of jam nuts 46 disposed in contiguous relation with the plate, at the opposite sides thereof. The plate 44, in practice, serves as a mounting for a plurality of electrical terminals, not designated, the purposes of which will hereinafter become more readily apparent.

Suspended from the support member 40 is a specimen holder 47. The specimen holder 47 includes a vertically oriented center post 48 rigidly connected to the support member 40 through a plurality of screws 50. The center post 48 is formed of a suitable rigid material, such as aluminum. The center post includes a diametrically extended bore, not designated, which receives a horizontally oriented suspension bar 52. The bar 52 is secured to the center post by suitable means including a setscrew 54. It is to be understood that the specimen holder 47 is of a rigid configuration and that the specimen holder 47 is rigidly connected with the support member 40 so that relative motion between the elements of the specimen holder 47 and the support member 40 is precluded.

Mounted at equidistances along the suspension bar 52 there is a plurality of spacers 55 formed of a suitable material such as Micarta or the like. The spacers 55 are secured in place on the suspension bar 52 employing suitable screws, not designated, and serve to position specimens 56, shown in phantom. It should be apparent that the intervals between the spacers 55 are such as to accommodate a mounting of a plurality of specimens which, in practice, comprise bands of elastomeric material. As shown, the specimens 56 are of unequal breadth, however, the dimension of the specimens form no part of the invention. Therefore, the specimens may be of uniform dimensions.

Mounted beneath the specimen holder 47, in coplanar relation therewith, there is a specimen holder, generally designated 60. The specimen holder 60 also includes a vertically oriented center post 62 having a bore, not designated, extended diametrically therethrough for receiving in coplanar parallelism with the suspension bar 52 a suspension bar 64. A plurality of spacers 66, also formed of Micarta, are mounted on the suspension bar 64 at intervals corresponding to the intervals at which the spacers 55 are mounted on the suspension bar 52. Thus a mounting of the specimens 56 between the suspension bars 52 and 64 is facilitated.

The center post 62 also is formed of Micarta, in order to reduce its heat transfer capabilities, and extends downwardly through a sleeve 68 seated in and projected through the bottom wall 20 of the chamber 18. The sleeve 68 serves as a bearing sleeve for the center post 62. Thus the specimen holder 60 is supported for reciprocation in coplanar relation with the specimen holder 47 and functions to subject specimens 56 suspended between the suspension bars 52 and 64 to sinusoidal strain as reciprocation is imparted to the specimen holder. The sleeve 68 is, where so desired, designed to accommodate lateral oscillation of the center post 62 in order to reduce wear.

Reciprocation is imparted to each of the specimen holders 60 through a drive train, generally designated 70, connected thereto. Each of the drive trains 70 includes a disk 72 having provided on its face a helical array of bores 74. The disk 72 is connected to the lowermost end of the center post 62 through a vertically oriented pitman link 76. The pitman link 76 is connected at one end to the disk 72 by a knuckle-pin 78 extended through the lowermost end of the pitman link 76 and received within a selected one of the bores 74 while the opposite end of the pitman link 76 is connected to the lowermost end of the center post 62 by a knuckle pin 80. This pin is extended through the center post and received within a suitably formed aperture, not designated, suitably provided in the center post.

It should be apparent that the total throw of the center post 62 is determined by the positional relationship of the knuckle-pin 78 with the center of the disk 72 as the disk is driven in rotation. Moreover, it is also important to appreciate that each of the disks 72 is driven in rotation at a predetermined angular rate which differs from the rates at which the remaining disks are driven whereby the specimens suspended between the suspension bars 52 and 64 at the various test stations 30 cyclically elongate and contract at different strain rates.

Each of the drive trains 70, provided for driving the disk 72 at the test stations 30, includes a drive shaft. The drive shafts, for descriptive purposes, are herein designated 82a through 82e. Each of the drive shafts 82a through 82e is received in and supported by suitable journal bearings, designated 84, arranged in coaxially spaced relation.

Mounted on the first-in-line drive shaft, designated 82a, is a worm gear 86 which is, in turn, meshed with a worm 88 driven by an electrically energizable motor 90. The worm is connected with the motor through a suitable clutch 92 so that as the motor 90 is energized, the worm 88 is driven for imparting rotary motion to the worm gear 86, which motion, in turn, is transmitted to the disk 72 mounted on the drive shaft 82a.

Also mounted on the drive shaft 82a is a drive sheave 93 which is connected, through a speed reduction unit 94, in a driving relationship with driven sheave 95 mounted on the adjacent drive shaft 82b.

As a practical matter, the speed reduction unit 94 includes a sheave 96 connected in a driven relationship with the sheave 93 through a suitable endless belt 97. The sheave 96 is mounted on a suitably supported idler shaft 98. Also mounted upon the shaft 98 there is a drive sheave 99 which is coupled in a driving relationship with the sheave 95 through a suitable endless belt 100.

The drive shaft 82b is connected with the drive shaft 82c through a speed reduction unit 102, while the shaft 82c, in turn, is connected with the shaft 82d, through a speed reduction unit 104 and, finally, the shaft 82d is connected with the drive shaft 82e through a speed reduction unit 106.

The speed reduction units 102, 104, and 106 are similar in their design, construction and function to the speed reduction unit 94, therefore, a detailed description of the speed reduction units 102 through 106 is omitted in the interest of brevity. However, it is to be understood that the speed reduction units serve to reduce the angular velocities of the drive shafts 82b through 82e by a given factor. As presently employed, the speed reduction units each serve to reduce angular velocities by a factor of ten. For example, where the drive shaft 82a is driven at 2 rpm, the drive shaft 82e will be driven at 0.0002 rpm. Thus it is possible to reciprocate the specimen holders 60 for the test stations 30 over a cyclic frequency range of five decades.

In practice, temperature control is desirable. Therefore, the chamber 18 is provided with a heat transfer unit 108, including a plurality of fins, not designated, whereby heat transfer, either into or from the chamber 18, is facilitated for purposes of maintaining temperature control within the chamber. While the specific heat transfer unit employed forms no part of the invention, the unit employed includes a plurality of coils through which a fluid is conducted.

Figure 5:
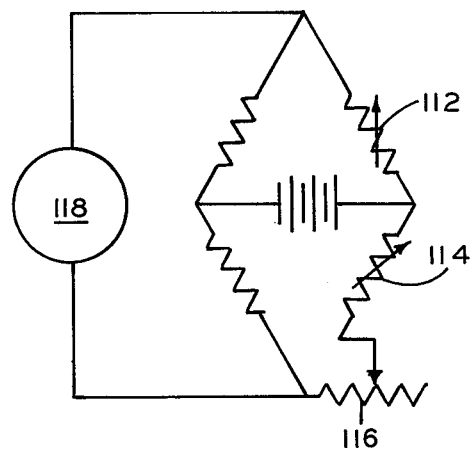
FIG. 5 is a diagrammatic view illustrating a bridge circuit employed in providing a read-out through which the fatigue life for elastomeric materials subjected to strain by the machine is determined.

Mounted on the support member 40 is a strain gauge, generally designated 110, which serves to detect strain induced in the specimens 56 as reciprocation is imparted to the specimen holders 60. The strain gauge 110 includes variable resistor components 112 and 114 interconnected within a bridge circuit, FIG. 5, not designated. The resistor 112 is mounted on the support member 40 and serves to detect strain induced in response to motion imparted to the specimen holder 60 while the resistor 114 serves to detect thermal strain. A potentiometer 116 is interconnected between the bridge circuit and a read-out 118 whereby the bridge circuit may be adjusted to compensate for thermal strain within the support member 40. Since the operation of strain gauges is well understood, a more detailed description of the strain gauge 110 is omitted in the interest of brevity. However, it is to be understood that the strain gauge is connected through suitable leads 120 to terminals mounted on the plate 44. From the terminals mounted on the plate 44 intelligence pickoff leads 122 extend to terminal blocks 124 at which an electrical connection is made for connecting the test stations 30 with a read-out device and/or a recorder, not shown.

Finally, while not shown, it is to be understood that Teflon sleeves are provided where so desired, in concentric relation with the suspension bars 52 and 64 in order to preclude abrasion between the bars and the specimens.

OPERATION

It is believed that in view of the foregoing description, the operation of the device will readily be understood and it will be briefly reviewed at this point.

With the machine 10 assembled in the manner hereinbefore described, it is possible to simultaneously monitor the fatigue life for a plurality of elastomeric specimens cyclically subjected to strain over a range of frequencies and amplitudes.

Simply by adjusting the pitman links 76, in order to vary total excursion, the strain rate at the test stations can be varied. For example, during each rotation of each of the disks 72 specimens 56 suspended at the test station 30 associated therewith will undergo both increasing strain and decreasing strain. If the radial distance between the axis of rotation for the disk 72 and the axis for knuckle-pin 78 is two and one-half inches the total excursion of the associated specimen holder 60 is 5 inches. Should the disk 72 rotate at 2 rpm, the specimens are elongated five inches in each one-quarter minute so that the strain rate is twenty inches per minute. That is to say, the specimens are subjected to increasing strain for two cycles and to decreasing strain for two cycles during each minute in which the disk is rotated. The remaining disks provide strain rates of 2.0, 0.2, 0.02, 0.002 and 0.0002 inches per minute so that a monitoring of the specimens over a spread of five decades is facilitated, provided the distances between the axis of the disks 72 and the knuckle-pins 78 are uniform.

The output of the strain gauge 110, temperature compensated, is fed to a suitable recorder. When all of the specimens are fully stretched, the strain gauge output will be of a maximum magnitude, however, as specimens fall, the strain detected by the strain gauge 110 is reduced proportionally and indicated by the read-out 118. If desired, the intelligence is recorded by a recorder to which the test stations are connected.

In view of the foregoing, it should readily be apparent that the machine of the instant invention provides a practical solution to the problem of determining fatigue life for a plurality of elastomeric specimens simultaneously subjected to cyclic strain.

Although the invention has been herein shown and described in what is conceived to be the most practical and preferred embodiment, it is recognized that departures may be made therefrom within the scope of the invention, which is not to be limited to the illustrative details disclosed.

What is claimed is:

1. An improved machine for use in determining the term of fatigue life for a plurality of elastomeric specimens simultaneously subjected to cyclic strain over a range of frequencies comprising:
    A. a plurality of test stations arranged in juxtaposition;
    B. specimen support means located at each of said test stations for supporting in suspension a plurality of specimens of elastomeric materials; and
    C. tensioning means arranged in coplanar relation with said specimen support means at each of said stations for periodically applying to the specimens supported at each of said stations tensile force of a magnitude suitable for cyclically subjecting the specimens to sinusoidal strain including means for selectively varying the amplitude of the strain to which the specimens are subjected at each of said stations, whereby monitoring of fatigue life over a range of strain amplitudes if facilitated.

2. The machine of claim 1 further comprising means for establishing common temperature conditions at said plurality of test stations.

3. The machine of claim 1 further comprising means for detecting failure of said specimens at each of said test stations, whereby determination of the term of the fatigue life for the specimens is facilitated.

4. The machine of claim 3 wherein said specimen support means located at each of said test stations comprises a first transversely oriented bar supported in a substantially fixed relationship with said machine, and said tensioning means comprises a second elongated bar disposed in substantial parallelism with said first elongated bar and means for imparting to said second bar rectilinear reciprocation at a rate unique with respect to the rate at which rectilinear reciprocation is imparted to the second elongated bar at each of the remaining test stations of said plurality of test stations.

5. The machine of claim 4 wherein said tensioning means further includes a plurality of disks arranged in a coplanar relation, a drive shaft supporting each of said disks for rotation about the axis thereof, and a drive train interconnecting the drive shaft for simultaneously driving said disks at constant rates of rotation, the rate of rotation for each of said disks being unique with respect to the rate at which the remaining disks of said plurality of disks are rotated.

6. The machine of claim 5 wherein the rate of rotation for each of said disks differs by a factor of ten from the rate at which each adjacent disk is rotated.

7. The machine of claim 6 wherein the means for detecting failure of said specimens at each of said test station includes a strain gauge connected with said first horizontal bar and adapted to be stressed in response to tensile force applied to the specimens.

8. The machine of claim 7 wherein means for establishing common temperature conditions at said plurality of test stations includes means defining an hermetically sealable chamber within which said test stations are arranged.

* * * * *